United States Patent
Park et al.

(10) Patent No.: US 9,690,908 B2
(45) Date of Patent: Jun. 27, 2017

(54) METHOD FOR MANAGING MEDICINE TAKING BY A USER TERMINAL IN A SYSTEM COMPRISING THE USER TERMINAL, A SERVER, AND A MEDICINE CONTAINER, AND THE USER TERMINAL PERFORMING THE METHOD

(71) Applicant: LG ELECTRONICS INC., Seoul (KR)

(72) Inventors: Myungeun Park, Seoul (KR); Dongkyu Seo, Seoul (KR); Heeseong Yun, Seoul (KR); Jiyoung Huh, Seoul (KR); Heejin Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 186 days.

(21) Appl. No.: 14/217,742

(22) Filed: Mar. 18, 2014

(65) Prior Publication Data
US 2015/0178469 A1    Jun. 25, 2015

(30) Foreign Application Priority Data
Dec. 19, 2013    (KR) .......................... 10-2013-0159405

(51) Int. Cl.
| G06Q 50/22 | (2012.01) |
| G06Q 50/24 | (2012.01) |
| G06F 19/00 | (2011.01) |
| G06Q 10/10 | (2012.01) |
| A61J 7/04 | (2006.01) |

(52) U.S. Cl.
CPC .......... *G06F 19/3456* (2013.01); *A61J 7/049* (2015.05); *A61J 7/0409* (2013.01); *A61J 7/0418* (2015.05); *A61J 7/0427* (2015.05); *A61J 7/0481* (2013.01); *G06Q 10/1095* (2013.01); *A61J 2205/10* (2013.01)

(58) Field of Classification Search
CPC ............ G06F 19/3462; G06F 19/3456; G06F 19/322; G06F 19/3406; G06F 19/3418; G06F 19/323; G06F 19/327; G06F 19/3468; G06F 19/366; G06Q 50/22; G06Q 50/24; A61J 2200/30; A61J 2205/10; A61J 2205/70; A61J 7/02
See application file for complete search history.

(56) References Cited

U.S. PATENT DOCUMENTS

| 2008/0059228 A1* | 3/2008 | Bossi .................. G06F 19/3418 705/2 |
| 2009/0294521 A1* | 12/2009 | de la Huerga .......... A61J 1/035 235/375 |
| 2014/0184772 A1* | 7/2014 | Hanina ............... G06F 19/3456 348/77 |

* cited by examiner

*Primary Examiner* — Maroun Kanaan
(74) *Attorney, Agent, or Firm* — Lee, Hong, Degerman, Kang & Waimey

(57) ABSTRACT

A method of managing a taking medicine, user terminal for the same and system therefor are disclosed. The present invention includes detecting an identification information of a medicine using a user terminal, transmitting a taking medicine information of the medicine from a sever to the user terminal using the detected identification information, setting a user's taking medicine schedule in the user terminal in accordance with the taking medicine information. Accordingly, a user is guided in taking a medicine. And, it is able to check whether a medicine has been taken.

14 Claims, 22 Drawing Sheets

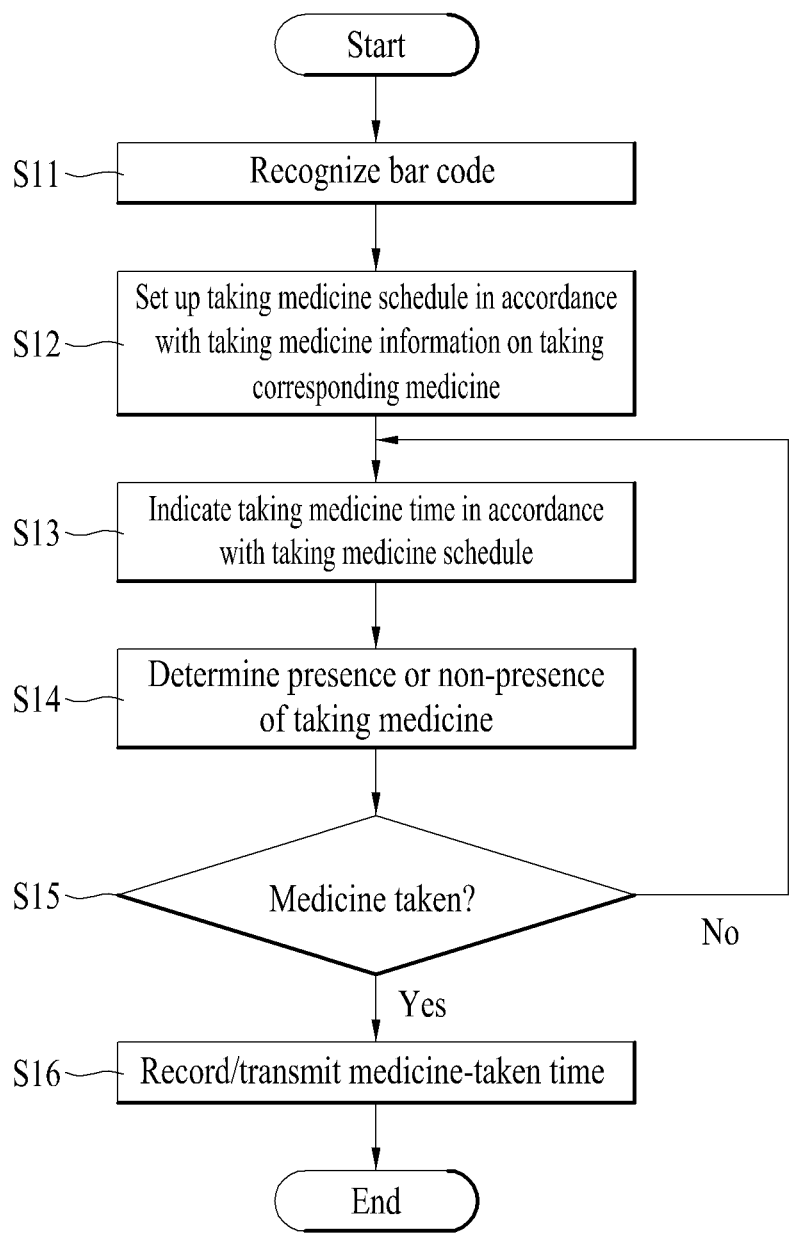

It's time to take
a medicine. It should be taken
30 minutes after meal.

This medicine prescribed
on January 15,
2013 is past its
expiration date.

(a)            (b)

METHOD FOR MANAGING MEDICINE TAKING BY A USER TERMINAL IN A SYSTEM COMPRISING THE USER TERMINAL, A SERVER, AND A MEDICINE CONTAINER, AND THE USER TERMINAL PERFORMING THE METHOD

Pursuant to 35 U.S.C. §119(a), this application claims the benefit of earlier filing date and right of priority to Korean Application No. 10-2013-0159405, filed on Dec. 19, 2013, the contents of which are hereby incorporated by reference herein in their entirety.

BACKGROUND OF THE INVENTION

Field of the Invention

The present invention relates to a taking medicine management, and more particularly, to a method of managing a taking medicine, user terminal for the same and system therefor. Although the present invention is suitable for a wide scope of applications, it is particularly suitable for guiding a user in a taking medicine and checking whether a medicine has been taken.

Discussion of the Related Art

Generally, even a healthy man takes medicines several times a year. And, a chronic invalid should take medicines periodically for a long term. Since the medicines composed of different chemical components, each of the medicines has different absorbing and decomposing processes in a human body and a taking medicine time is mostly determined in advance. Hence, in order to achieve a proper taking medicine effect, it is important to take medicine at a time determined in a predetermined interval depending on ingredients of a medicine and duration of a medical effect.

A medical doctor for prescribing medication or a pharmacist for filling a prescription usually leaves instructions of a taking medicine time and method suitable for living patterns of ordinary people like 'after rising', 'before meal', 'after meal', 'before sleeping' and the like for a medication time. Yet, such taking medicine instructions are verbally described by doctors or pharmacists and then depend on memory and attention of a medicine taker in a taking medicine process. Hence, it is difficult to expect an effective taking medicine in accordance with a taking medicine schedule unless each medicine taker pays attention. Particularly, it is not easy for people living in this busy modern society to take medicines properly at a determined time by carrying medicines when going out. Moreover, since a child or an old person may have attention weaker than that of an ordinary person, it may be actually difficult for the child or old person to take medicines punctually and periodically in accordance with a taking medicine schedule. Moreover, the child or old person may not remember a presence or non-presence of a taking medicine of her/his own, whereby medicines may be incorrectly abused.

In order to solve the above-mentioned problems, a separate record chart has been used to assist the taking medicine management. In this case, the separate record chart may include a node, a memo or the like for a user to record a taking medicine event after each taking medicine. Yet, since a taking medicine management using such a record chart is handwritten by a person, it may be difficult to achieve efficient managements. If a user handwrites a taking medicine event on a record chart each taking medicine, an omission or mistake in writing is highly possible. Even if a person tending the sick records a taking medicine event, it may be actually difficult for the person to record every taking medicine event.

Recently, a medicine chest for sorting and receiving medicines supposed to be taken at the determined times is used. This medicine chest is more advantageous than recording a taking medicine event on a record chart in checking whether a medicine is taken. Yet, it is difficult to carry the medicine chest due to a size or weight of the medicine chest. And, the medicine chest needs a job of sorting medicines by taking medicine times. Moreover, if the medicine chest is used, a medicine may be incorrectly received due to a mistake in sorting the medicines. Moreover, since it is necessary to use a separate alarm and the like in order for the medicine chest to inform a user of a taking medicine time, the medicine chest is still insufficient for the systematic taking medicine managements. So, the demand for a method of informing a user of a taking medicine effectively and checking a presence or non-presence of the taking medicine is rising.

SUMMARY OF THE INVENTION

Accordingly, embodiments of the present invention are directed to a method of managing a taking medicine, user terminal for the same and system therefor that substantially obviate one or more problems due to limitations and disadvantages of the related art.

One object of the present invention is to provide a method of managing a taking medicine, user terminal for the same and system therefor, by which a user can be informed of a taking medicine.

Another object of the present invention is to provide a method of managing a taking medicine, user terminal for the same and system therefor, by which whether a medicine has been taken can be checked.

Technical tasks obtainable from the present invention are non-limited by the above-mentioned technical tasks. And, other unmentioned technical tasks can be clearly understood from the following description by those having ordinary skill in the technical field to which the present invention pertains.

Additional advantages, objects, and features of the invention will be set forth in the disclosure herein as well as the accompanying drawings. Such aspects may also be appreciated by those skilled in the art based on the disclosure herein.

To achieve these objects and other advantages and in accordance with the purpose of the invention, as embodied and broadly described herein, a method of managing a taking medicine according to one embodiment of the present invention includes the steps of detecting an identification information of a medicine using a user terminal, transmitting a taking medicine information of the medicine from a sever to the user terminal using the detected identification information, and setting a user's taking medicine schedule in the user terminal in accordance with the taking medicine information.

Preferably, the identification information includes a bar code. Preferably, the taking medicine information includes information on at least one of a taking medicine period, a taking medicine count, a taking medicine time and a taking medicine method of the medicine.

Preferably, the method further includes the step of outputting an alarm for informing the user of a time for taking the medicine in accordance with the set taking medicine schedule using the user terminal. Preferably, the method further includes the step of determining a presence or non-presence of the taking medicine of the user in accordance with the set taking medicine schedule using the user terminal.

More preferably, the user terminal outputs a voice message for asking the user of the presence or non-presence of the taking medicine at a taking medicine time designated in accordance with the taking medicine schedule and determines the presence or non-presence of the taking medicine of the user by recognizing a voice of the user. More preferably, the user terminal determines the presence or non-presence of the taking medicine of the user depending on a signal outputted from a sensor configured to detect whether a lid of a container of the medicine is opened or closed.

More preferably, the method further includes the step of adjusting the set taking medicine schedule in accordance with a time for the user to take the medicine using the user terminal. Preferably, the method further includes the step of outputting an alarm for informing the user of an expiration date of the medicine using the user terminal.

In another aspect of the present invention, a user terminal according to one embodiment of the present invention includes a detecting unit configured to detect an identification information of a medicine, a communication unit configured to transceiving information, and a control unit controlling the communication unit to receive a taking medicine information of the medicine from a server using the detected identification information, the control unit setting a taking medicine schedule of a user in accordance with the received taking medicine information.

Preferably, the control unit controls to output an alarm for informing the user of a time for taking the medicine in accordance with the set taking medicine schedule. Preferably, the control unit determines a presence or non-presence of the taking medicine of the user in accordance with the set taking medicine schedule.

More preferably, the control unit records an information on the presence or non-presence of the taking medicine of the user in the user terminal and transmits the information on the presence or non-presence of the taking medicine of the user to the server. More preferably, the control unit adjusts the set taking medicine schedule in accordance with a time for the user to take the medicine using the user terminal.

In another aspect of the present invention, a taking medicine management system according to one embodiment of the present invention includes a server configured to store a taking medicine information per medicine and a user terminal detecting an identification information of a medicine, the user terminal receiving the taking medicine information of the medicine from the server using the detected identification information, the user terminal setting a taking medicine schedule of a user in accordance with the received taking medicine information.

In another aspect of the present invention, a method of managing a taking medicine according to another embodiment of the present invention includes the steps of detecting an identification information of a medicine using a user terminal, transmitting a taking medicine information of the medicine to a medicine container of the medicine using the detected identification information, setting a taking medicine schedule of a user in the medicine container in accordance with the transmitted taking medicine information, and outputting an alarm for informing the user of a time for taking the medicine from the medicine container in accordance with the set taking medicine schedule.

In another aspect of the present invention, a medicine container according to one embodiment of the present invention includes a communication unit for communication with a user terminal, a signal output unit outputting an alarm, and a control unit setting a taking medicine schedule of a user in accordance with a taking medicine information of a medicine transmitted from the user terminal, the control unit controlling the signal output unit to output the alarm for informing the user of a time for taking the medicine in accordance with the set taking medicine schedule.

In a further aspect of the present invention, a taking medicine management system according to another embodiment of the present invention includes a user terminal detecting an identification information of a medicine, the user terminal transmitting a taking medicine information of the medicine using the detected identification information and a medicine container setting a taking medicine schedule of a user in accordance with the taking medicine information transmitted from the user terminal, the medicine container outputting an alarm for informing the user of a time for taking the medicine in accordance with the set taking medicine schedule.

Accordingly, the present invention provides the following effects and/or advantages.

First of all, according to at least one embodiments of the present invention, since a user is automatically informed of a taking medicine through a user's terminal and whether a medicine is taken is checked through the user's terminal, taking medicine managements can be performed systematically and accurately.

Secondly, the present invention can give instructions of joint-use prohibited medicines and medicine expiration dates, thereby preventing medicine abuse and misuse.

Effects obtainable from the present invention may be non-limited by the above mentioned effect. And, other unmentioned effects can be clearly understood from the following description by those having ordinary skill in the technical field to which the present invention pertains.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. The above and other aspects, features, and advantages of the present invention will become more apparent upon consideration of the following description of preferred embodiments, taken in conjunction with the accompanying drawing figures. In the drawings:

FIG. 3 is a flowchart to describe an operation of the taking medicine management system shown in FIG. 1;

DETAILED DESCRIPTION OF THE INVENTION

Reference will now be made in detail to embodiments of the present invention, examples of which are illustrated in the accompanying drawings.

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts. A mobile terminal according to the present invention is described in detail with reference to the accompanying drawings as follows.

In the following description, reference will now be made in detail to the preferred embodiments of the present invention, examples of which are illustrated in the accompanying drawings. First of all, terminologies or words used in this specification and claims are not construed as limited to the general or dictionary meanings and should be construed as the meanings and concepts matching the technical idea of the present invention based on the principle that an inventor is able to appropriately define the concepts of the terminologies to describe the inventor's intention in best way. The embodiment disclosed in this disclosure and configurations shown in the accompanying drawings are just one preferred embodiment and do not represent all technical idea of the present invention. Therefore, it is understood that the present invention covers the modifications and variations of this invention provided they come within the scope of the appended claims and their equivalents at the timing point of filing this application.

In the following description, a taking medicine management system according to a $1^{st}$ embodiment of the present invention is explained in detail with reference to FIG. 1.

Figure 1:
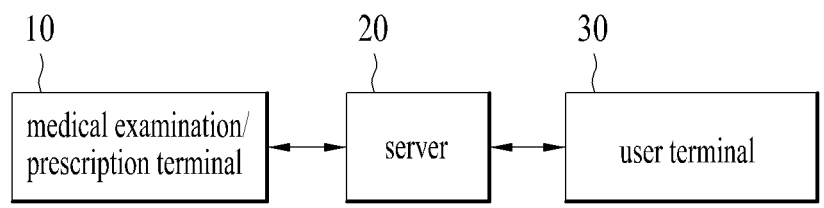
FIG. 1 is a block diagram of a taking medicine management system according to a $1^{st}$ embodiment of the present invention.

FIG. 1 is a block diagram of a taking medicine management system according to a $1^{st}$ embodiment of the present invention.

Referring to FIG. 1, a taking medicine management system according to the present invention may include a medical examination/prescription terminal 10, a server 20 and a user terminal 30.

The medical examination/prescription terminal 10 is provided for a doctor to input a disease and symptom of a patient (i.e., a user), a list of medicines prescribed for the patient, a period for taking each of the medicines, a count of taking medicines, a taking medicine time, a taking medicine method, warnings and the like. The medical examination/prescription terminal 10 is connected to the server 20 by wire/wireless and then transmits the informations inputted by the doctor to the server 20. And, the doctor can check the informations saved in the server 20 through the medical examination/prescription terminal 10.

The server 20 receives information from the medical examination/prescription terminal 10 and then stores the received information. In particular, the server 20 stores a user information including a name, social security number (or ID), address, phone number of each patient and the like, an information on diseases and symptoms of each patient, an information on a taking medicine history of each patient, an information on a list of medicines prescribed to each patient, a taking medicine information (e.g., a prescription) on taking medicine periods, taking medicine count, taking medicine times, taking medicine methods, warnings of the prescribed medicines, and the like. And, the server 20 can store information on a general taking medicine count, taking medicine time, taking medicine method, warnings of each medicine provided by a manufacturer as well.

The user terminal 30 may preferably include such a mobile terminal capable of wireless communication as a smartphone, a laptop, a tablet and the like, by which the present invention may be non-limited. For instance, the user terminal 30 may include a terminal capable of wired communication. Regarding primary functions, the user terminal 30 receives a taking medicine information for a corresponding user from the server 20 and then sets up a taking medicine schedule of the user using the received taking medicine information. To this end, the user terminal 30 has the following configuration.

Figure 2:
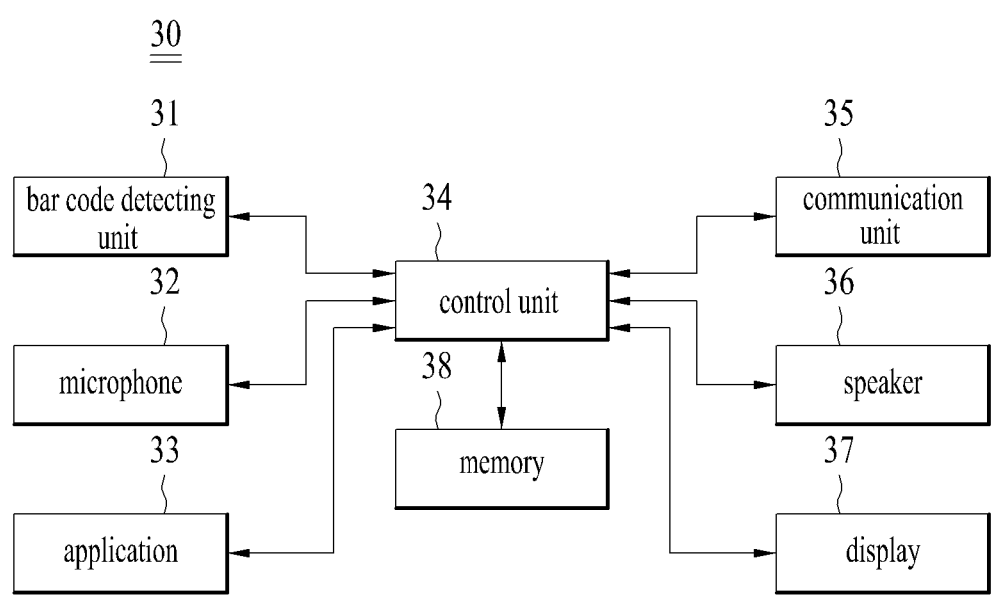
FIG. 2 is a block diagram of a user terminal shown in FIG. 1.

FIG. 2 is a block diagram of the user terminal shown in FIG. 1.

Referring to FIG. 2, the user terminal 30 may include a bar code detecting unit 31, a microphone 32, an application 33, a control unit 34, a communication unit 35, a speaker 36, a display 37 and a memory 38.

The bar code detecting unit 31 is configured to detect a bar code that is an identification information inscribed on a medicine container. The bar code detecting unit 31 can include a camera or a bar code scanner. In case that the bar code detecting unit 31 includes the camera, the bar code detecting unit 31 photographs an image including the bar code inscribed on the medicine container and then provides the control unit 34 with a bar code image to interpret the bar code. On the other hand, in case that the bar code detecting unit 31 includes the bar code scanner, the bar code detecting unit 31 reads the bar code using a laser beam, converts the bar code to an electric signal, and then provides the electric signal to the control unit 34.

The microphone 32 is configured to detect a user's voice, and more particularly, a user's voice that indicates whether the user has taken a medicine.

The application 33 is provided to activate and control a series of operations for setting a taking medicine schedule and providing a user with a taking medicine method. In doing so, the operations are implemented by the control unit 34.

The communication unit 35 is connected to the server 20 through such a wireless communication network for remote wireless communication as 3G, LTE and the like. Of course, it is possible for the communication unit 35 to be connected to the server 20 through a wired communication network.

The memory 38 stores an information on diseases and symptoms of a user, an information on a taking medicine history of the user, an information on a list of medicines prescribed to the user, a taking medicine information on taking medicine periods, taking medicine count, taking medicine times, taking medicine methods, warnings of the prescribed medicines, and the like. And, the memory 38 stores an expiration date of a medicine.

The control unit 34 controls all components included in the user terminal 30 to perform operations required for the application 33. For instance, the control unit 34 controls the bar code detecting unit 31 to detect a bar code. And, the control unit 34 controls the communication unit 35 to transmit the detected bar code or information included in the bar code to the server 20 and receive user's taking medicine information from the server 20.

The control unit 34 controls the memory 38 to store the received taking medicine information, sets up a user's taking medicine schedule using the taking medicine information, and then saves the taking medicine schedule in the memory 38.

The control unit 34 controls the speaker 36 and/or the display 37 to output an alarm for informing a user of a time for taking a medicine or an expiration date of the medicine in accordance with the set taking medicine schedule as at least one of a sound, an illumination and a message. Optionally, it is able to use such a system for indicating a medicine taking time or expiration date as a vibration and the like as well as a sound, an illumination and a message.

The control unit 34 determines whether a user has taken a medicine in accordance with the set taking medicine schedule. In particular, the control unit 34 can make a determination based on a user's input through a user interface (not shown in the drawing) or a user's voice detected through the microphone 32. For instance, the control unit 34 outputs a voice message, which asks a user whether the user has taken a medicine at a taking medicine time designated in accordance with the set taking medicine schedule, through the speaker 36 and then determines whether the user has taken the medicine by recognizing a user's response to the voice message, i.e., a user's voice. Subsequently, the control unit 34 controls an information on a presence or non-presence of user's taking medicine to be saved in the memory 38 and transmits the information to the server 20 through the communication unit 35.

The control unit 34 can adjust the taking medicine schedule depending on a time at which a user has taken a medicine. For instance, the control unit 34 measures a difference between a taking medicine time designated by the taking medicine schedule and an average time at which a user has actually taken a medicine. The control unit 34 then adjusts the taking medicine schedule in accordance with the measured difference. And, the control unit 34 can adjust the taking medicine schedule in consideration of a medicine-taken time per weekday, a meal time and the like inputted by a user.

Operations of the taking medicine management system shown in FIG. 1 are described in detail with reference to FIGS. 3 to 6 as follows.

FIG. 3 is a flowchart to describe an operation of the taking medicine management system shown in FIG. 1.

Referring to FIG. 3, the user terminal 30 detects and recognizes an identification information inscribed on a container of a medicine [S11]. In doing so, although a user can directly input a serial number of the medicine to the user terminal 30. Preferably, for user's convenience, a bar code is detected using the bar code detecting unit 31. In this case, the bar code may include information indicating a country, a manufacturer, a medicine, an expiration date and the like.

Once the bar code is recognized by the user terminal 30, a taking medicine management for the user starts. To this end, the control unit 34 of the user terminal 30 sets up a user's taking medicine schedule using a taking medicine schedule of the medicine corresponding to the detected bar code. In this case, the taking medicine schedule designates a taking medicine period (e.g., 1 month, etc.) of the corresponding medicine, a taking medicine count per day (e.g., 3 times a day, etc.), taking medicine times of the medicines (e.g., 9 A.M., 1:30 P.M., 19:00 PM, etc.) and the like. A detailed method of setting up a taking medicine schedule is described as follows.

First of all, for example of a method of setting up a taking medicine schedule, the control unit 34 controls the communication unit 35 to transmit the detected bar code or the information included in the bar code to the server 20 together with a user identification information including at least one of a name, social security number (or ID) and phone number of a user. Subsequently, the server 20 checks information related to the corresponding user only using the user identification information and then provides the user terminal 30 with the taking medicine information of the medicine corresponding to the bar code. And, the control unit 34 sets up a user's taking medicine schedule using the taking medicine information transmitted by the server 20.

For another example of setting up a taking medicine schedule, the control unit 34 reads the taking medicine information of the medicine corresponding to the detected bar code among taking medicine informations of medicines previously saved in the memory 38 and then sets up a user's taking medicine schedule using the corresponding taking medicine information.

Meanwhile, the bar code information transmitted to the server 20 or the information included in the bar code transmitted to the server 20 is saved in the server 20 and then enables a doctor to check whether a user has received the corresponding medicine, whether the corresponding medicine coincides with a prescribed medicine, whether the medicine received by the user is prohibited from being jointly used with a prescribed medicine. The doctor can add a taking medicine guide for side effect possible medicines or upload a new prescription to the server 20. The user terminal 30 saves the list of the joint-use prohibited medicines and the added taking medicine guide and is then able to provide the user with the saved list and guide. Since the memory 38 stores the list of the joint-use prohibited medicines, in case that a user purchases a new medicine, the control unit 34 determines the joint-use prohibited medicines using the detected bar code and then informs the user of the corresponding determination.

The controller 34 controls the memory 38 to store the bar code, the information included in the bar code, the received taking medicine information and the set taking medicine schedule and is then able to determine whether a prescribed medicine matches a prescribed medicine using the bar code or the information included in the bar code.

Thereafter, the control unit 34 controls the speaker 36 and the display 37 to output an alarm for informing the user of a time for taking a medicine or an expiration date of the medicine in accordance with the set taking medicine schedule.

Figures 4A, 4B:
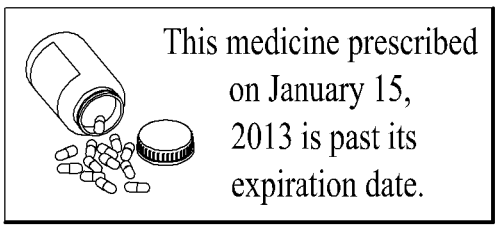
FIG. 4A is a diagram for one example of a taking medicine alarm according to the present invention.
FIG. 4B is a diagram for one example of an expiration date indication according to the present invention.

FIG. 4A is a diagram for one example of a taking medicine alarm according to the present invention. And, FIG. 4B is a diagram for one example of an expiration date indication according to the present invention.

Referring to FIG. 4A and FIG. 4B, the control unit 34 provides a user with a voice or message indicating a taking medicine time (e.g., 9:00 AM) and a taking medicine method (e.g., take it 30 minutes after a meal) at a time for a taking medicine [FIG. 4A] and also provides the user with a voice or a message for indicating an expiration date [FIG. 4B]. Particularly, the control unit 34 controls the speaker 36 and the display 37 to inform the user of the taking medicine method on an initial alarm or every taking medicine timing point. Regarding the expiration date, the control unit 34 controls the speaker 36 and the display 37 to inform the user of the expiration date after reception of the corresponding medicine or on arrival of the expiration date. Moreover, since information indicating expiration dates of medicines is included in a bar code saved in the memory 38, the user is able to refer the bar code to the memory 38 for the expiration dates of the previously registered medicines.

Referring now to FIG. 3, the control unit 34 determines a presence or non-presence of a user's taking medicine on or after an alarm [S14]. A detailed method of determining a presence or non-presence of the user's taking medicine (i.e., whether the user has taken the medicine) is described as follows.

First of all, for one example of a method of determining a presence or non-presence of a user's taking medicine, the control unit 34 determines a presence or non-presence of the user's taking medicine based on a taking medicine time inputted through a user interface (not shown in the drawing) by the user.

Secondly, for another example of a method of determining a presence or non-presence of a user's taking medicine, the control unit 34 determines a presence or non-presence of the user's taking medicine in a manner of outputting a voice message (e.g., 'Did you take a medicine?), which asks the user whether the user has taken a medicine, at a taking medicine time designated by the set taking medicine schedule through the speaker 36 and then recognizing a user's response to the voice message, i.e., a user's answer through the microphone 32. If the user answers with 'Yes' or 'O.K.' in response to the voice message, the control unit 34 determines that the user has taken the medicine [S15]. On the contrary, if the user does not respond to the voice message, the control unit 34 outputs an alarm and a voice message for asking the user of a presence or non-presence of the user's taking medicine to the user again after predetermined duration [S13, S14].

Thereafter, the control unit 34 saves the information on a presence or non-presence of the user's taking medicine in the memory 38 and then transmits the information to the server 20 through the communication unit 35 [S16]. Therefore, the user can refer to the memory 38 for a taking medicine history of the user. And, medical personnel confirm a presence or non-presence of the user's taking medicine through the server 20 and are able to utilize it as a reference material for a next medical examination and treatment.

The control unit 34 can adjust the taking medicine schedule in accordance with a time at which a user has taken a medicine. A method of adjusting a taking medicine time is described in detail as follows.

Figure 6:
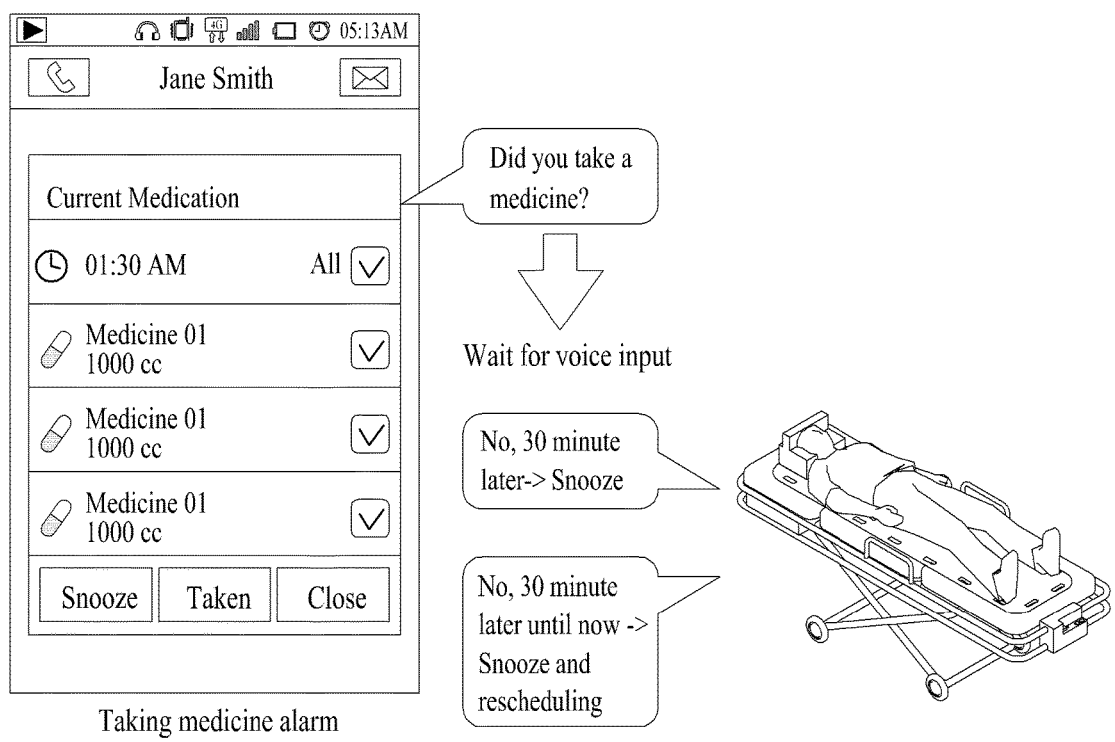
FIG. 6 is a diagram for one example of a method of adjusting a taking medicine schedule according to the present invention.

First of all, for one example of a method of adjusting a taking medicine time, referring to FIG. 6, if a user gives an answer 'Snooze 30 minutes later' to a voice message for querying a presence or non-presence of a user's taking medicine, the control unit 34 recognizes the user's answer and then adjusts an alarm time into '30 minutes later'. Moreover, if a user gives an answer 'Snooze 30 minutes and continue' to the voice message, the control unit 34 determines that the user wants adjustment of a taking medicine time inputted by a doctor and then adjusts the taking medicine schedule. For instance, if a taking medicine time is set to 1:30, it can be adjusted into 2:00 that is 30 minutes after 1:30. Thereafter, an alarm and a voice message are outputted at the adjusted time '2:00'.

Secondly, for another example of a method of adjusting a taking medicine time, the control unit 34 measures a difference between a taking medicine time designated by the taking medicine schedule and an average time for a user to actually take a medicine. If the measured difference deviates from an allowed values (e.g., 1 hour), the control unit 34 substitutes the designated taking medicine time with the actually medicine-taken average time. This is expressed as follows.

$$|\text{Designated taking medicine time} - \text{Average of actually medicine-taken times}| \geq \epsilon$$

Thus, once the user's taking medicine schedule is adjusted, the control unit 34 saves the adjusted taking medicine in the memory 38 and transmits it to the server 20. Moreover, the control unit 34 informs the user of the taking medicine time in accordance with the adjusted taking medicine schedule.

In the following description, a taking medicine management system according to a $2^{nd}$ embodiment of the present invention is explained with reference to FIG. 7.

Figure 7:
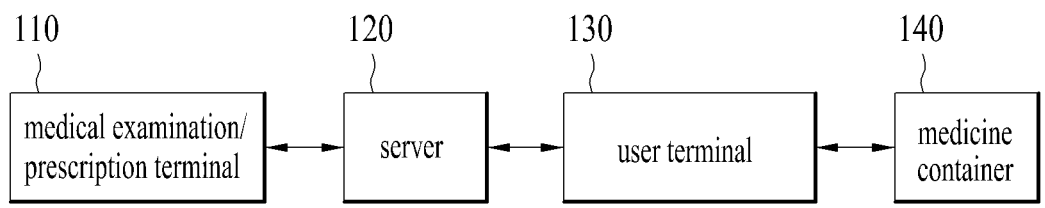
FIG. 7 is a block diagram of a taking medicine management system according to a $2^{nd}$ embodiment of the present invention.

FIG. 7 is a block diagram of a taking medicine management system according to a $2^{nd}$ embodiment of the present invention.

Referring to FIG. 7, a taking medicine management system according to a $2^{nd}$ embodiment of the present invention may include a medical examination/prescription terminal 110, a server 120, a user terminal 130 and a medicine container 140. In this case, the medical examination/prescription terminal 110 and the server 120 have the same configurations of the former terminal 10 and server 20 of the $1^{st}$ embodiment.

The user terminal 130 may preferably include such a mobile terminal capable of short and long range wireless communications as a smartphone, a laptop, a tablet and the like, by which the present invention may be non-limited. For instance, the user terminal 130 may include a terminal capable of wired communication. Regarding primary functions, the user terminal 130 receives a taking medicine information for a corresponding user from the server 120, sets up a taking medicine schedule of the user using the received taking medicine information, and transmits the received taking medicine information to the medicine container 140. To this end, the user terminal 130 has the following configuration.

Figure 8:
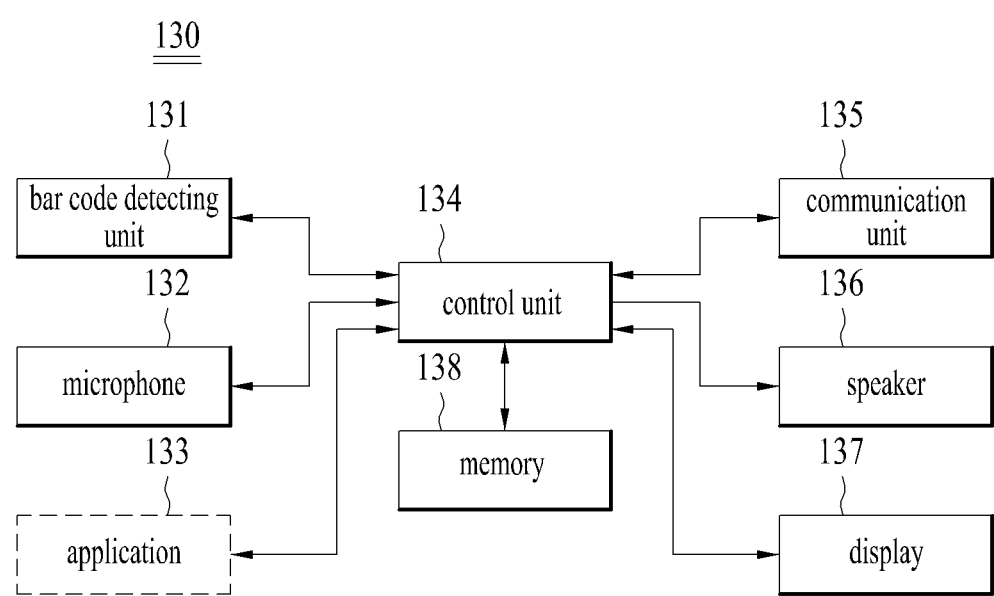
FIG. 8 is a block diagram of a user terminal shown in FIG. 7.

Referring to FIG. 8, the user terminal 130 may include a bar code detecting unit 131, a microphone 132, an application 133, a control unit 134, a communication unit 135, a speaker 136, a display 137 and a memory 138. In this case, the bar code detecting unit 131, the microphone 132, the speaker 136, the display 137 and the memory 138 are configured identical to those of the 1$^{st}$ embodiment.

The application 133 is provided to activate and control a series of operations for setting a taking medicine schedule and providing a user with a taking medicine method. In doing so, the operations are implemented by the control unit 134. Particularly, the application controls the user terminal 130 and the medicine container 140 to operate in a manner of being linked to each other.

The communication unit 135 is connected to the server 120 through such a wireless communication network for remote wireless communication as 3G, LTE and the like. Of course, it is possible for the communication unit 135 to be connected to the server 120 through a wired communication network. Moreover, the communication unit 135 is connected to the medicine container 140 using such a short range wireless communication system as Bluetooth, Wi-Fi and the like for the communication with the medicine container 140.

The control unit 134 controls all components included in the user terminal 130 to perform operations required for the application 313. In the same manner of the former control unit 34 of the 1$^{st}$ embodiment, the control unit 134 controls the bar code detecting unit 131 to detect a bar code. And, the control unit 134 controls the communication unit 135 to transmit the detected bar code or information included in the bar code to the server 120 and receive user's taking medicine information from the server 120.

Moreover, the control unit 134 controls the communication unit 135 to transmit the received taking medicine information to the medicine container 140 and also controls the user terminal 130 to set up a user's taking medicine schedule using the taking medicine information. And, the control unit 134 controls the set taking medicine schedule to be saved in the memory 138.

The control unit 134 controls the speaker 136 and/or the display 137 to output an alarm for informing a user of a time for taking a medicine or an expiration date of the medicine in accordance with the set taking medicine schedule as at least one of a sound, an illumination and a message. Optionally, it is able to use such a system for indicating a medicine taking time or expiration date as a vibration and the like as well as a sound, an illumination and a message.

The control unit 134 determines whether a user has taken a medicine in accordance with the set taking medicine schedule. In doing so, the control unit 134 can make a determination based on at least one of a user's input through a user interface (not shown in the drawing), a user's voice detected through the microphone 132 and an output signal from a sensor 147 configured to detect whether a lid of the medicine container 140 is open or closed. Subsequently, the control unit 134 controls information on a presence or non-presence of user's taking medicine to be saved in the memory 138 and transmits the information to the server 120 through the communication unit 135.

The control unit 134 can adjust the taking medicine schedule depending on a time at which a user has taken a medicine. For instance, the control unit 134 measures a difference between a taking medicine time designated by the taking medicine schedule and an average time at which a user has actually taken a medicine. The control unit 134 then adjusts the taking medicine schedule in accordance with the measured difference. And, the control unit 134 provides the adjusted taking medicine schedule to the medicine container 140 and the server 120.

The medicine container 140 may include a container of a medicine purchased by a user or a separate container for receiving a purchased medicine therein. If the medicine container 140 includes the container of the purchased medicine, it may include an identification information of the corresponding medicine. If the medicine container 140 simply includes the medicine receiving container, it may not include an identification information.

Figure 9:
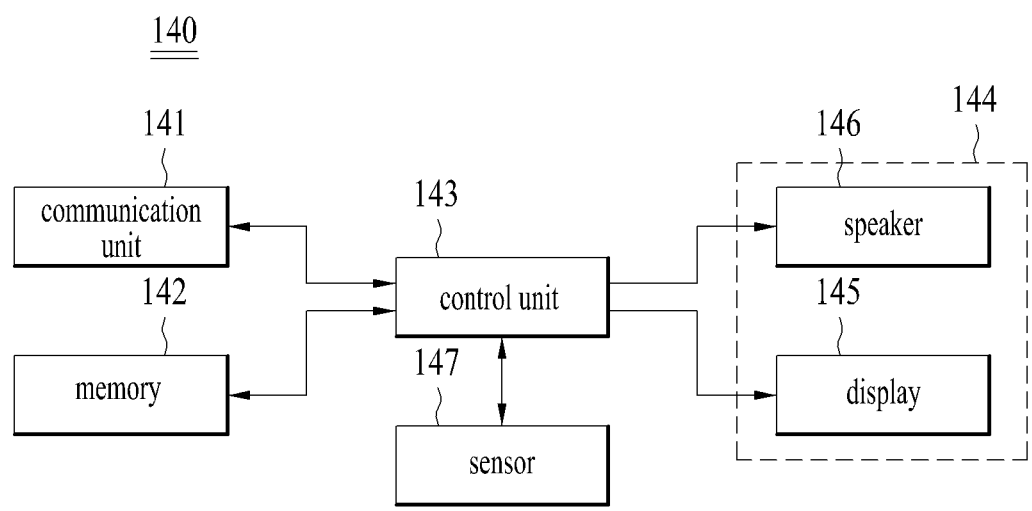
FIG. 9 is a block diagram of a medicine container shown in FIG. 7.

FIG. 9 is a block diagram of the medicine container shown in FIG. 7.

Referring to FIG. 9, the medicine container 140 may include a communication unit 141, a memory 142, a control unit 143, a signal output unit 144 and a sensor 147.

The communication unit 141 is connected to the user terminal 130 through such a short range wireless communication system as Bluetooth, Wi-Fi and the like. The memory 142 stores a taking medicine information of a medicine provided by the user terminal 130, an expiration date of the medicine provided by the user terminal 130 and a user's taking medicine schedule.

The control unit 143 controls the memory 142 to store the taking medicine information and the expiration date and also controls the user's taking medicine schedule to be set up in the medicine container 140 using the taking medicine information. The control unit 143 controls the set taking medicine schedule to be saved in the memory 142. If the taking medicine schedule is adjusted by the user terminal 130, the control unit 143 controls the adjusted taking medicine schedule to be saved in the memory 142.

The control unit 143 controls the signal output unit 144, which includes a speaker 146 and/or a display 145, to output an alarm for informing a user of a time for taking a medicine or an expiration date of the medicine in accordance with the set taking medicine schedule as at least one of a sound, an illumination and a message. In doing so, the control unit 143 controls the display 145 to output an illumination differing in color depending on a content of the alarm. Likewise, it is able to use such a system for indicating a medicine taking time or expiration date as a vibration and the like as well as a sound, an illumination and a message.

The sensor 147 detects whether a user has taken a medicine after the alarm and then outputs a signal for indicating a presence or non-presence of the detection. To this end, the sensor 147 may include a switch sensor or a contact sensor. The control unit 143 determines the number of medicines remaining in the medicine container 140 by counting the number of the user's taking medicine events and may be set to inform the user terminal 130 of the determined number of the medicines.

Operations of the taking medicine management system according to the 2$^{nd}$ embodiment of the present invention are described in detail with reference to FIG. 10 as follows.

Figure 10:
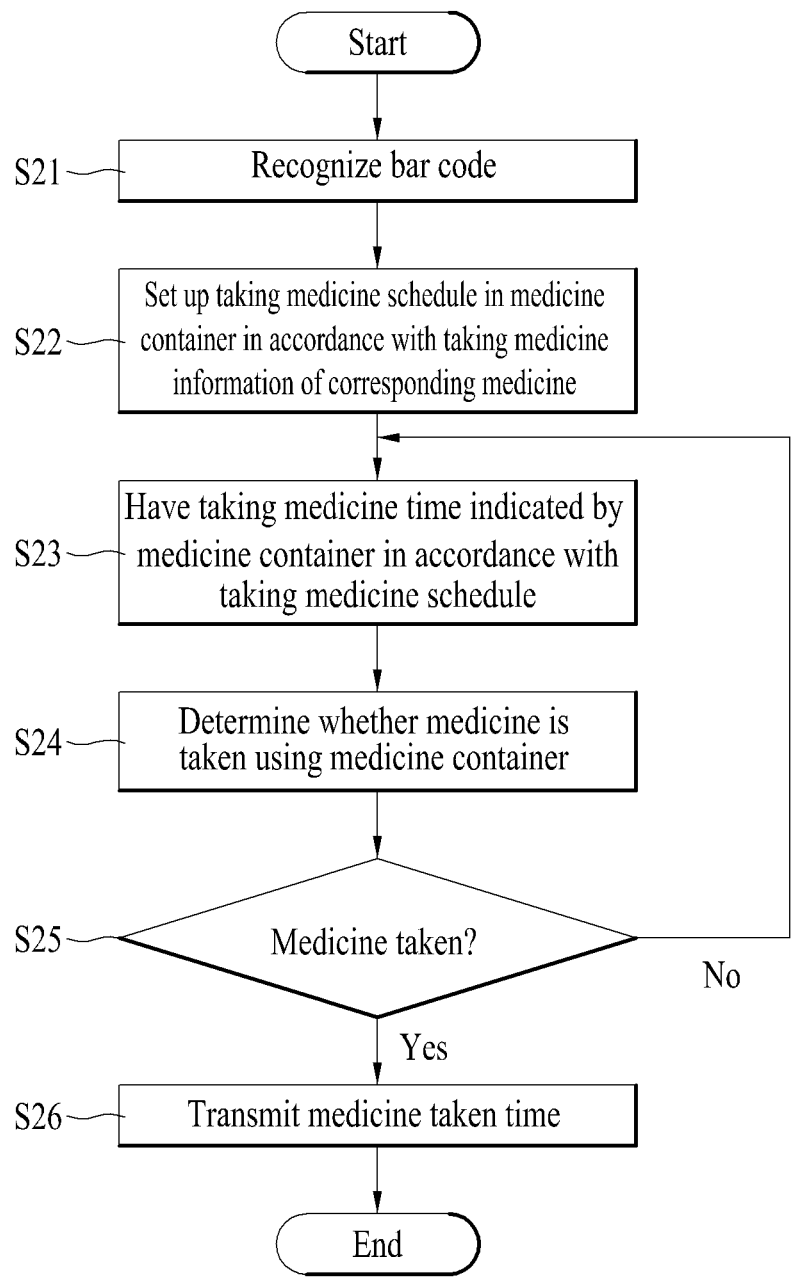
FIG. 10 is a flowchart to describe an operation of the taking medicine management system shown in FIG. 7.
Figure 11:
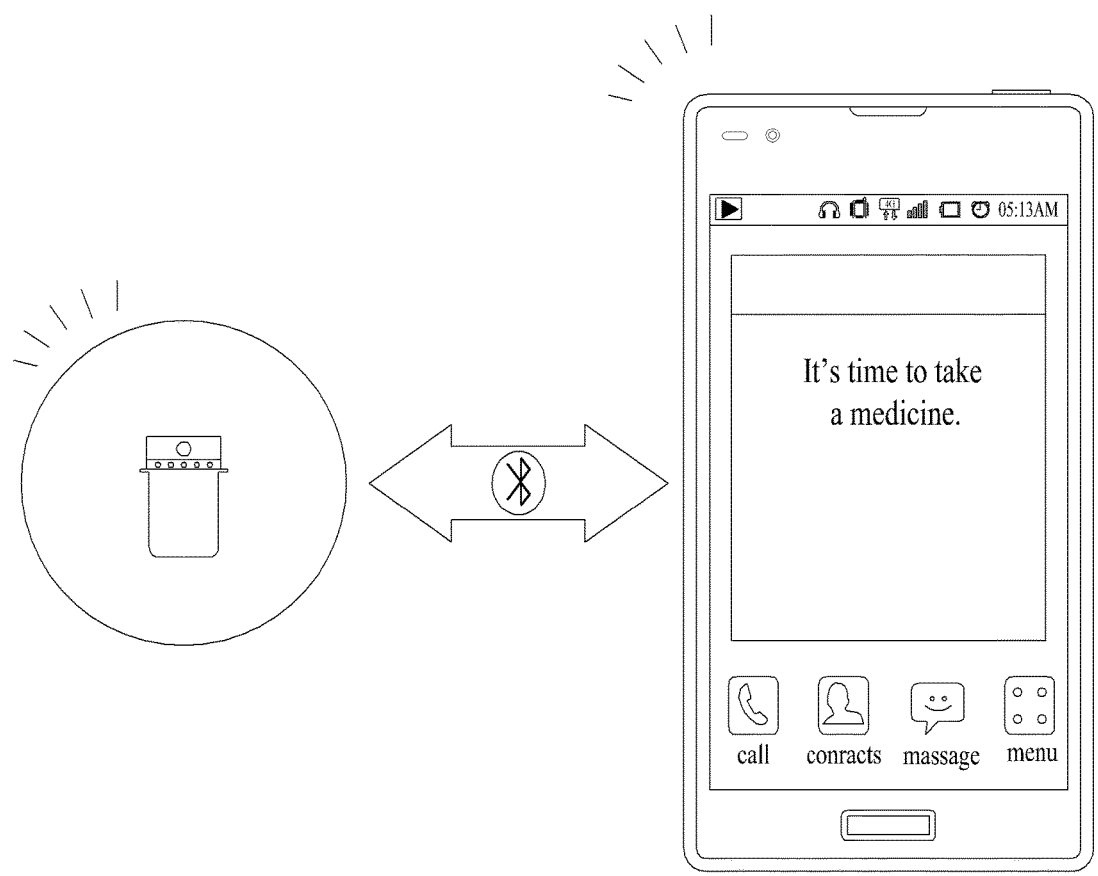
FIG. 11 is a diagram of a user terminal and medicine container shown in FIG. 7.

FIG. 10 is a flowchart to describe an operation of the taking medicine management system shown in FIG. 7.

Referring to FIG. 10, like the 1st embodiment, the user terminal 130 detects and recognizes an identification information inscribed on a container of a medicine [S21]. In doing so, although a user can directly input a serial number of the medicine to the user terminal 30. Preferably, for user's convenience, a bar code is detected using the bar code detecting unit 31.

Once the bar code is recognized by the user terminal 130, a taking medicine management for the user starts. To this end, the control unit 134 of the user terminal 130 sets up a user's taking medicine schedule using a taking medicine schedule of the medicine corresponding to the detected bar code. Likewise, the control unit 143 of the medicine container 140 sets up a user's taking medicine schedule in the medicine container [S22]. In this case, the taking medicine schedule designates a taking medicine period (e.g., 1 month, etc.) of the corresponding medicine, a taking medicine count per day (e.g., 3 times a day, etc.), taking medicine times of the medicines (e.g., 9 A.M., 1:30 P.M., 19:00 PM, etc.) and the like. A detailed method of setting up a taking medicine schedule is described as follows.

First of all, for example of a method of setting up a taking medicine schedule, the control unit 134 controls the communication unit 135 to transmit the detected bar code or the information included in the bar code to the server 120 together with a user identification information including at least one of a name, social security number (or ID) and phone number of a user. Subsequently, the server 120 checks information related to the corresponding user only using the user identification information and then provides the user terminal 130 with the taking medicine information of the medicine corresponding to the bar code. Subsequently, the control unit 134 controls the communication unit 135 to transmit the taking medicine schedule to the medicine container 140 and sets up a user's taking medicine schedule in the user terminal 130 using the taking medicine information. And, the medicine container 140 sets up a user's taking medicine schedule using the taking medicine information as well.

For another example of setting up a taking medicine schedule, the control unit 134 reads the taking medicine information of the medicine corresponding to the detected bar code among taking medicine informations of medicines previously saved in the memory 138 and controls the communication unit 135 to transmit the taking medicine information to the medicine container 140 and sets up a user's taking medicine schedule in the user terminal 130 using the taking medicine information. And, the medicine container 140 sets up a user's taking medicine schedule using the taking medicine information as well.

Meanwhile, the bar code information transmitted to the server 120 or the information included in the bar code transmitted to the server 120 is saved in the server 120. Based on this, a doctor can add a taking medicine guide for side effect possible medicines or upload a new prescription to the server 120. The user terminal 130 saves the list of the joint-use prohibited medicines and the added taking medicine guide and is then able to provide the user with the saved list and guide. Since the memory 138 stores the list of the joint-use prohibited medicines, in case that a user purchases a new medicine, the control unit 134 can determine the joint-use prohibited medicines using the detected bar code.

The controller 34 controls the memory 138 to store the bar code, the information included in the bar code, the received taking medicine information and the set taking medicine schedule and is then able to determine whether a prescribed medicine matches a prescribed medicine using the bar code or the information included in the bar code. Likewise, the control unit 143 of the medicine container 140 saves the received taking medicine information and the set taking medicine schedule in the memory 142 as well.

Thereafter, the control unit 134 controls the speaker 136 and the display 137 to output at least one of a sound, an illumination and a message in order to inform the user of a time for taking a medicine or an expiration date of the medicine in accordance with the set taking medicine schedule. And, the control unit 143 of the medicine container 140 controls the speaker 146 and the display 145 to output at least one of a sound, an illumination and a message in order to inform the user of a time for taking a medicine or an expiration date of the medicine in accordance with the set taking medicine schedule. In doing so, it is possible for either the user terminal 130 or the medicine container 140 to be set for alarm. Each of the user terminal 130 and the medicine container 140 informs the user of a medicine taking method on an initial alarm or every taking medicine timing point. In case of the expiration date, each of the user terminal 130 and the medicine container 140 informs the user of the expiration date after the corresponding medicine has been received or if an expiration date comes. Moreover, the user is able to refer the bar code to the memory 138 for the expiration dates of the previously registered medicines.

Moreover, the control unit 134 determines a presence or non-presence of a user's taking medicine on or after an alarm [S24]. A detailed method of determining a presence or non-presence of the user's taking medicine (i.e., whether the user has taken the medicine) is described as follows.

First of all, for one example of a method of determining a presence or non-presence of a user's taking medicine, the control unit 134 determines a presence or non-presence of the user's taking medicine based on a taking medicine time inputted through a user interface (not shown in the drawing) by the user.

Figure 5:
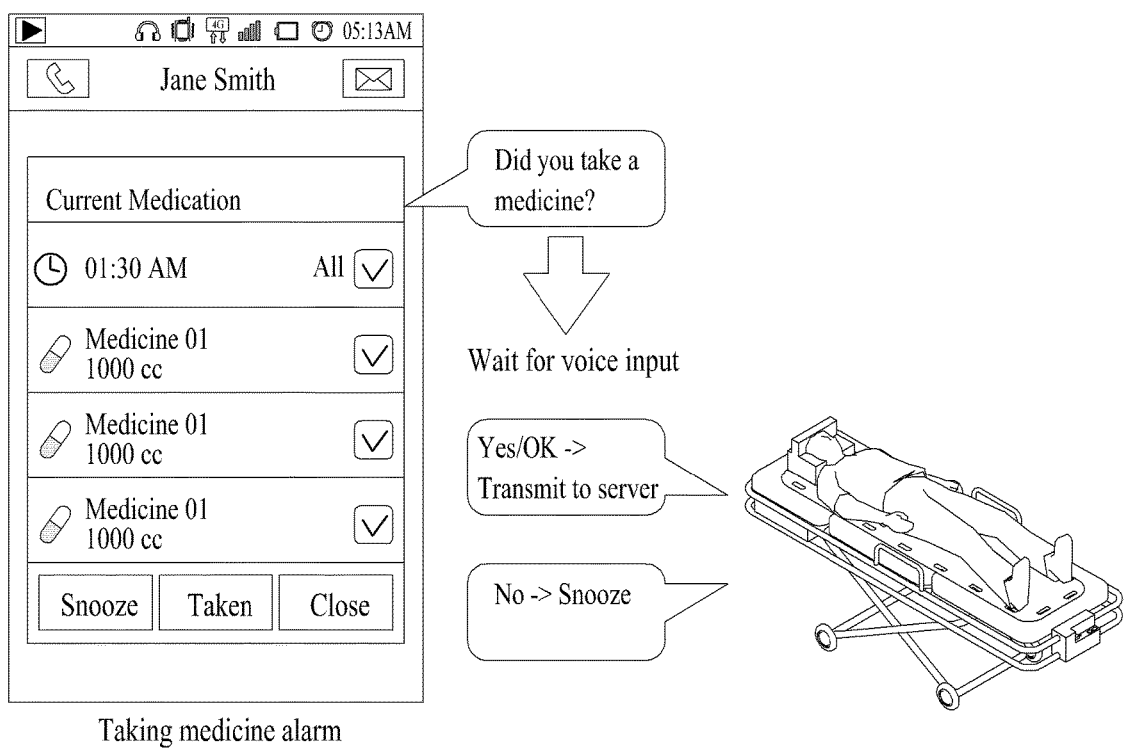
FIG. 5 is a diagram for one example of a method of determining whether a user has taken a medicine according to the present invention.

Secondly, for another example of a method of determining a presence or non-presence of a user's taking medicine, as shown in FIG. 5, the control unit 134 determines a presence or non-presence of the user's taking medicine in a manner of outputting a voice message (e.g., 'Did you take a medicine?), which asks the user whether the user has taken a medicine, at a taking medicine time designated by the set taking medicine schedule through the speaker 136 and then recognizing a user's response to the voice message, i.e., a user's answer through the microphone 132. If the user answers with 'Yes' or 'O.K.' in response to the voice message, the control unit 134 determines that the user has taken the medicine [S25]. On the contrary, if the user does not respond to the voice message, the control unit 134 outputs an alarm and a voice message for asking the user of a presence or non-presence of the user's taking medicine to the user again after predetermined duration [S23, S24].

Thirdly, for another example of a method of determining a presence or non-presence of a user's taking medicine, the control unit 134/143 can determine a presence or non-presence of a user's taking medicine based on an output signal from the sensor 147 configured to detect whether the lid of the medicine container 140 is open or closed. In particular, when the lid of the medicine container 140 is closed, the sensor 147 including a switch sensor or a contact sensor detects it and then informs the control unit 143 that lid of the medicine container 140 is closed. Subsequently, the control unit 143 informs the user terminal 130 of the corresponding information through the communication unit 141. The medicine container 140 may be set to periodically provide the user terminal 130 with a signal for indicating a presence or non-presence of a user's taking medicine on every predetermined time (e.g., every 2 hours, etc.). Alternatively, the medicine container 140 may be set to provide the user terminal 130 with a signal for indicating a presence or non-presence of a user's medicine taking only if the lid is closed.

Thereafter, the control unit 134 saves the information on a presence or non-presence of the user's taking medicine in the memory 138 and then transmits the information to the server 120 through the communication unit 135 [S26]. Therefore, the user can refer to the memory 138 for a taking medicine history of the user. And, medical personnel confirm a presence or non-presence of the user's taking medicine through the server 120 and are able to utilize it as a reference material for a next medical examination and treatment.

The control unit 134 can adjust the taking medicine schedule in accordance with a time at which a user has taken a medicine. A method of adjusting a taking medicine time is described in detail as follows.

First of all, for one example of a method of adjusting a taking medicine time, referring to FIG. 6, if a user gives an answer 'Snooze 30 minutes later' to a voice message for querying a presence or non-presence of a user's taking medicine, the control unit 134 recognizes the user's answer and then adjusts an alarm time into '30 minutes later'. Moreover, if a user gives an answer 'Snooze 30 minutes and continue' to the voice message, the control unit 134 determines that the user wants adjustment of a taking medicine time inputted by a doctor and then adjusts the taking medicine schedule.

For another example of a method of adjusting a taking medicine time, the control unit 134 measures a difference between a taking medicine time designated by the taking medicine schedule and an average time for a user to actually take a medicine. If the measured difference deviates from an allowed values (e.g., 1 hour), the control unit 134 substitutes the designated taking medicine time with the actually medicine-taken average time.

Thus, once the user's taking medicine schedule is adjusted, the control unit 134 saves the adjusted taking medicine in the memory 138 and transmits it to the server 120. And, the adjusted taking medicine schedule is provided to the medicine container 140 to be applied to the medicine container 140. The control unit 143 of the medicine container 140 saves the adjusted taking medicine schedule in the memory 142. Therefore, each of the user terminal 130 and the medicine container 140 can inform the user of the taking medicine time in accordance with the adjusted taking medicine schedule by reflecting the taking medicine schedule adjusted to synchronize the taking medicine schedule.

In the following description, one example of a remote photographing system according to the present invention is explained in detail with reference to FIG. 12.

Figure 12:
FIG. 12 is a diagram for one example of a remote photographing system according to the present invention.

FIG. 12 is a diagram for one example of a remote photographing system according to the present invention.

Referring to FIG. 12, a remote photographing system according to the present invention includes a $1^{st}$ terminal 210 and a $2^{nd}$ terminal 230. In this case, the $1^{st}$ terminal 210 and the $2^{nd}$ terminal 230 are connected to each other through a communication network 220.

The $1^{st}$ terminal 210 is a terminal of a user intending to have a medical examination and treatment. The $1^{st}$ terminal 210 preferably includes such a mobile terminal capable of wireless communication as a smartphone, a laptop, a tablet and the like, by which the present invention may be non-limited. And, the $1^{st}$ terminal 210 may include a terminal capable of wired communication. Regarding primary functions, the $1^{st}$ terminal 210 transmits a real-time image of a body part to be diagnosed to the $2^{nd}$ terminal 230 and then photographs a part to be diagnosed under the control of the $2^{nd}$ terminal 230.

Figure 13:
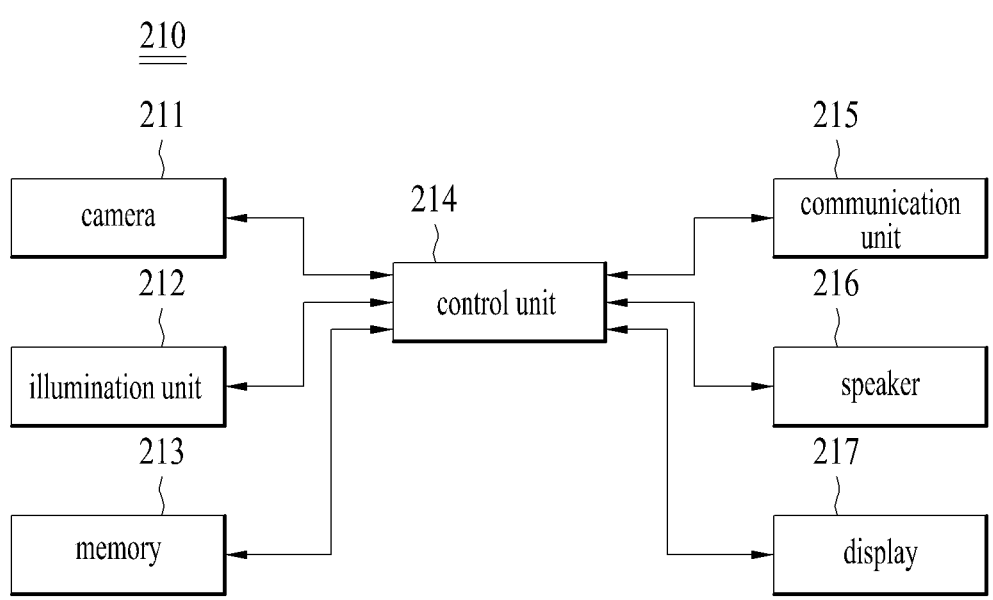
FIG. 13 is a block diagram for one example of a $1^{st}$ terminal shown in FIG. 12.

FIG. 13 is a block diagram for one example of the $1^{st}$ terminal shown in FIG. 12.

Referring to FIG. 13, the $1^{st}$ terminal 210 may include at least one camera 211, an illumination unit 212, a memory 213, a control unit 214, a communication unit 215, a speaker 216 and a display 217.

The camera 211 is configured to photograph a video image as well as a photo. When the photo or video is captured or photographed, the illumination unit 212 applies a flash or lightning to a photographed target.

The memory 213 stores the photographed photo or video, setting information of the camera 211, a prescription information (e.g., a list of prescribed medicines, taking medicine periods of medicines, a taking medicine time, a taking medicine method, warnings, etc.) transmitted from the $2^{nd}$ terminal 230, a history information on a video diagnosis and the like.

The communication unit 215 is connected to the $2^{nd}$ terminal 230 through such a communication network 220 as 3G, LTE and the like for a remote wireless communication. Of course, the communication unit 215 can be connected to the $2^{nd}$ terminal 230 through a wired communication network. Particularly, the communication unit 215 transmits a real-time image captured by the camera 211 to the $2^{nd}$ terminal 230 and receives signals and information for controlling the camera 211 from the $2^{nd}$ terminal 230.

The speaker 216 is configured to output sound/audio like a general mobile terminal. Particularly, the speaker 216 outputs a guide voice in response to a request made by the $2^{nd}$ terminal 230. The display 217 outputs a target captured by the camera 211 to a screen like a viewfinder and also outputs a photographed picture or video to the screen. The display 217 displays a guide for guiding moving and rotation directions of the camera 211 on the screen in response to a request made by the $2^{nd}$ terminal 230.

The control unit 214 controls all components included in the $1^{st}$ terminal 210. For instance, in response to a request made by the $2^{nd}$ terminal 230, the control unit 214 controls an operation of the camera 211 or changes the settings of the camera 211. Once a video diagnosis starts, the control unit 214 controls the illumination unit 212 to provide an illumination automatically.

The $2^{nd}$ terminal 230 is a terminal of medical personnel for a diagnosis and consultation. And, the $2^{nd}$ terminal 230 can have such a configuration capable of wireless/wire communication as a smartphone, a laptop, a tablet, a PC and the like. Regarding primary functions, the $2^{nd}$ terminal 230 outputs a real-time image transmitted from the $1^{st}$ terminal 210 to a screen and also outputs a user interface (UI) for controlling the camera 211 of the $1^{st}$ terminal 210 to the screen. And, the $2^{nd}$ terminal 230 controls the camera 211 by real time or provides the $1^{st}$ terminal 210 with control information for the real-time control, in response to an input applied by medical personnel through the user interface.

Figure 14:
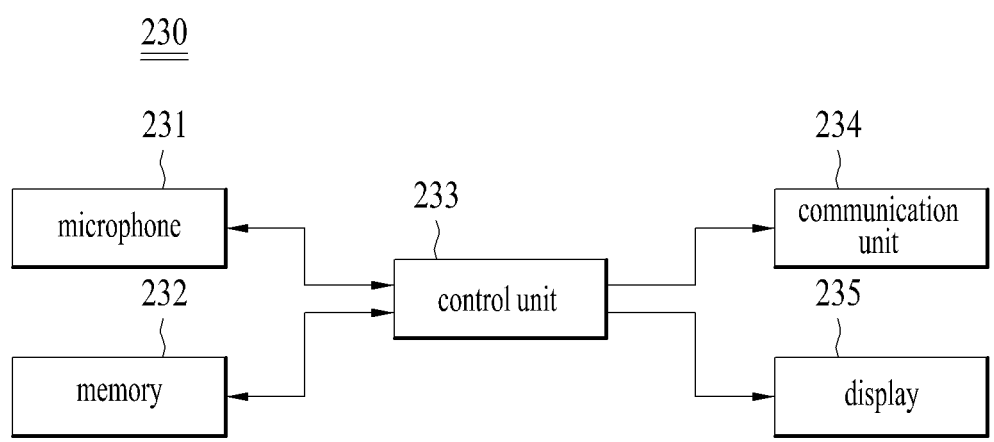
FIG. 14 is a block diagram for one example of a $2^{nd}$ terminal shown in FIG. 12.

To this end, referring to FIG. 14, the $2^{nd}$ terminal 230 may include a microphone 231, a memory 232, a control unit 233, a communication unit 234 and a display 235.

The microphone 231 is configured to detect sound and voice, and more particularly, voice of medical personnel in the course of a video diagnosis, like a general mobile terminal. The memory 232 stores photos and images transmitted from the 1$^{st}$ terminal 210, diseases and symptoms per patient, a video diagnosis history per patient, a prescription information per patient and the like. And, the communication unit 234 is connected to the 1$^{st}$ terminal 210 through a long distance wireless communication or a wired communication.

The display 235 outputs a real-time image transmitted from the 1$^{st}$ terminal 210 to a screen and also provides the screen with a user interface configured to control the camera 211 of the 1$^{st}$ terminal 210. In this case, the user interface provided to the screen may include at least one of a button, icon and menu for controlling an operation of the camera 211 or changing settings of the camera 211.

The control unit 233 controls the camera 211 by real time in accordance with an input applied through the user interface by the medical personnel or provides control information for controlling the camera 211 to the 1$^{st}$ terminal 210. For instance, the control unit 233 controls the 1$^{st}$ terminal 210 to capture an image photographed by the camera 211 and also controls a zoom function and illumination of the camera 211. The control unit 233 provides the screen of the 1$^{st}$ terminal 210 with a guide for guiding moving and rotation directions of the camera 211 and a guide line for guiding a position of a medically examined part in a captured image. And, the control unit 233 controls the 1$^{st}$ terminal 210 to display at least one of a scale and lattice for determining a size of the medically examined part on the captured image.

Operations of the remote photographing system shown in FIG. 12 are described in detail with reference to FIGS. 15 to 20 as follows.

Figure 15:
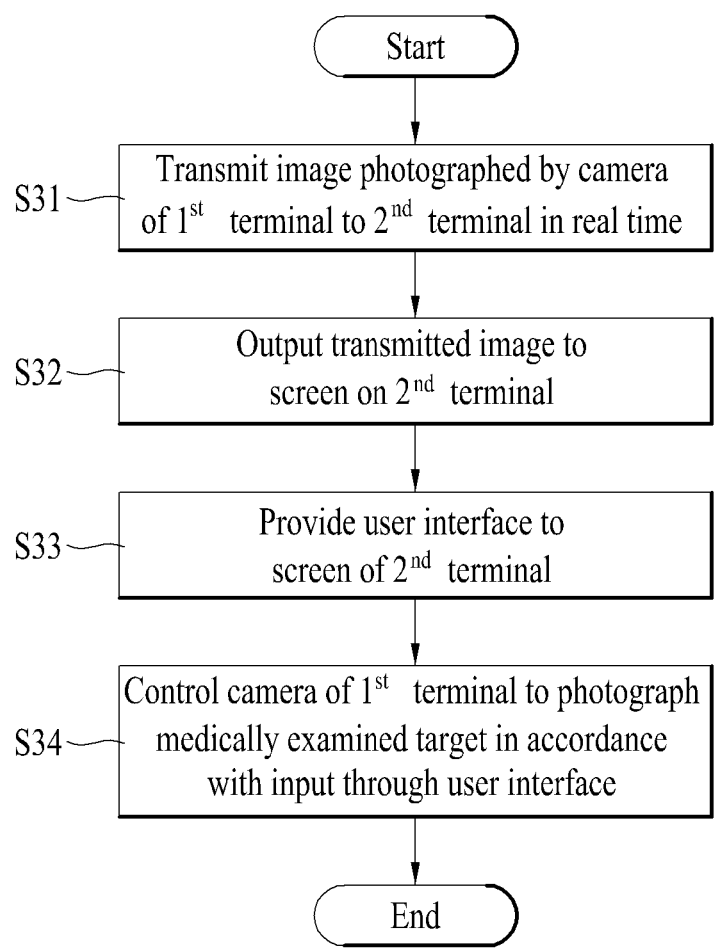
FIG. 15 is a flowchart to describe an operation of the remote photographing system shown in FIG. 12.
Figure 16:
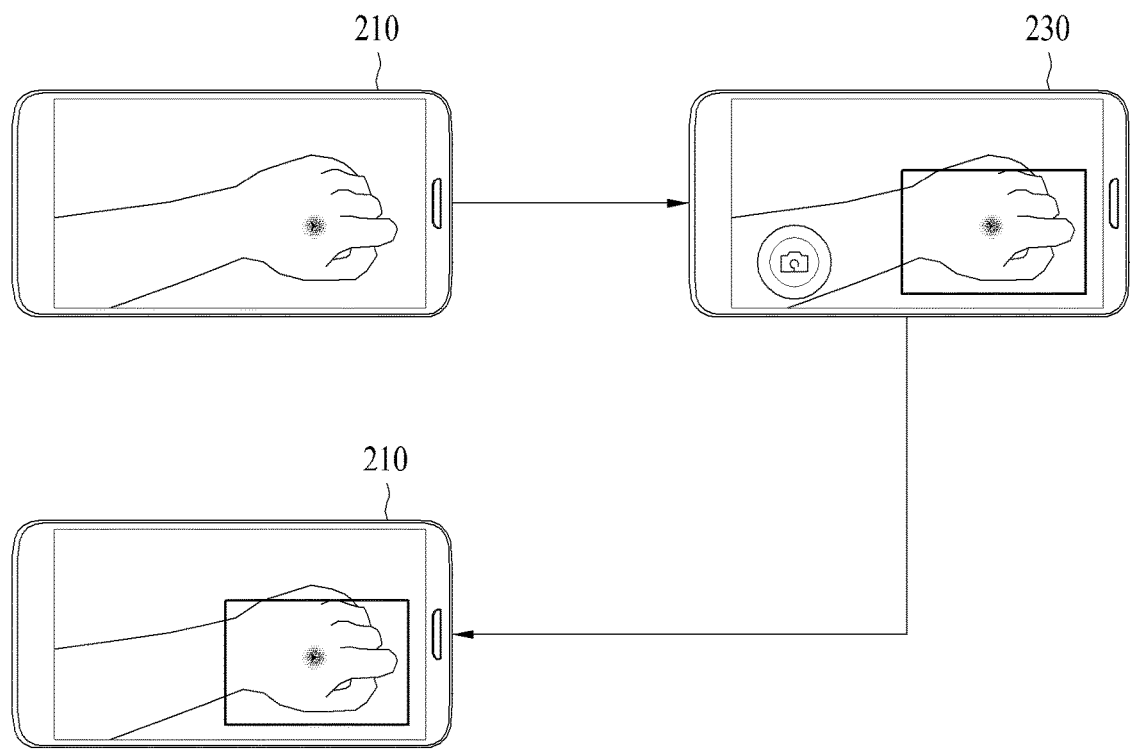
FIG. 16 is a diagram for a method of capturing a medical examination and treatment part using the remote photographing system shown in FIG. 12.
Figure 17:
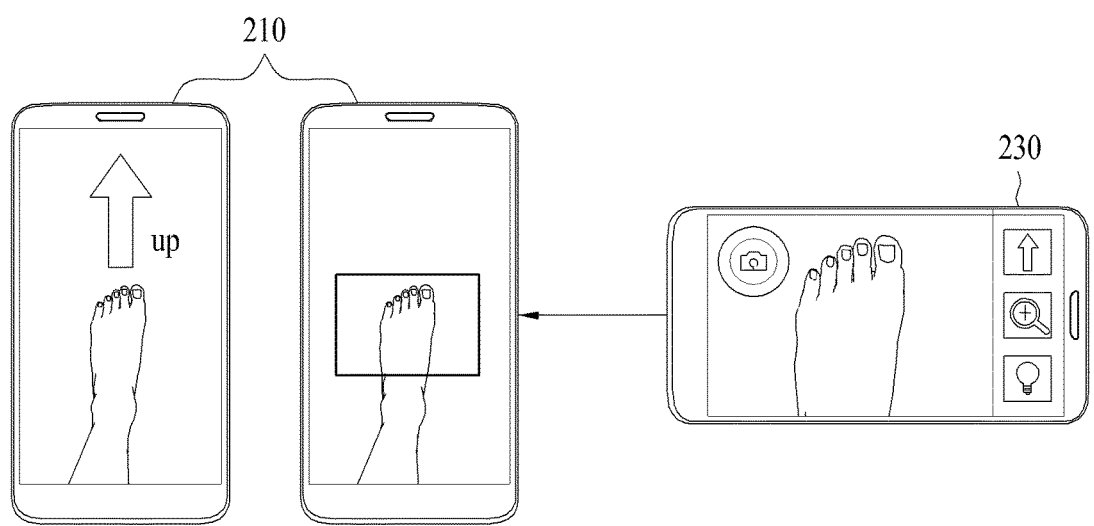
FIG. 17 is a diagram for a method of photographing a medical examination and treatment part using the remote photographing system shown in FIG. 12.
Figure 18:
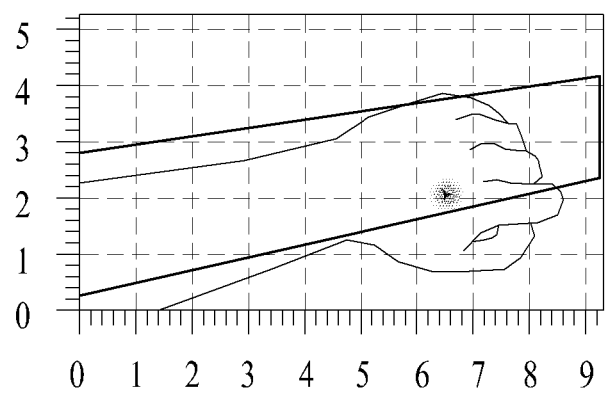
FIG. 18 is a diagram for one example of a guide line to indicate a location of a medical examination and treatment part in an image.

FIG. 15 is a flowchart to describe an operation of the remote photographing system shown in FIG. 12. FIG. 16 is a diagram for a method of capturing a medical examination and treatment part using the remote photographing system shown in FIG. 12. FIG. 17 is a diagram for a method of photographing a medical examination and treatment part using the remote photographing system shown in FIG. 12. And, FIG. 18 is a diagram for one example of a guide line to indicate a location of a medical examination and treatment part in an image.

Referring to FIG. 15, while a communication for remotely controlling the 1$^{st}$ terminal 210 is maintained, if a user controls the camera 211 to approach a part to be medically examined and treated, an image of the medically examined part captured by the camera 211 is transmitted to the 2$^{nd}$ terminal 230 by real time under the control of the control unit 214 [S31]. In doing so, the image captured by the camera 211, as shown in FIG. 16, is outputted to the screen of the display 217 of the 1$^{st}$ terminal 210 and is also outputted to the screen of the 2$^{nd}$ terminal 230 by real time [S32]. Therefore, medical personnel (e.g., a doctor, etc.) can check up the medically examined part of the user by real time through the 2$^{nd}$ terminal 230.

While the terminal 230 is outputting the image to the screen, it also provides a screen of the display 235 with a user interface for controlling the camera 211 [S33].

The 2$^{nd}$ terminal 230 changes the settings of the camera 211 in accordance with an input applied by the doctor through the user interface and also controls the camera 211 to photograph the medically examined part [S34]. Examples of this operation are described with reference to FIGS. 16 to 18 as follows.

For instance, referring to FIG. 16, the doctor selects all or a portion of a desired image from the image outputted to the screen of the 2$^{nd}$ terminal 230 using a touch or mouse and then gives a command for capturing the desired image using a capture button provided to the user interface. Once the user's command is inputted through the capture button, the 1$^{st}$ terminal 210 captures the image selected by the doctor. Subsequently, the 1$^{st}$ terminal 210 saves the captured image in the memory 213 and also transmits it to the 2$^{nd}$ terminal 230. Thereafter, the photo and image transmitted to the 2$^{nd}$ terminal 230 are saved in the memory 232. Thus, the doctor directly photographs images by remotely controlling the 1$^{st}$ terminal 210, thereby being able to manage a history, previous treatments, recovery progress and the like of the medically examined part such as a wound and the like in direct. Moreover, since photos or images of a specific part in various directions are saved in the 2$^{nd}$ terminal 230, the doctor can make an accurate diagnosis through the saved photos or images.

Referring to FIG. 17, if a doctor selects an icon in an arrow shape of a user interface provided to the screen of the 2$^{nd}$ terminal 230, a guide (e.g., an arrow, a text, etc.) for guiding moving and rotation directions of the camera 211 is displayed on the screen of the 1$^{st}$ terminal 210 and a voice guide (e.g., 'apply a camera in top direction') is also outputted through the speaker 216.

While the doctor is watching an image outputted to the screen of the 2$^{nd}$ terminal 230, if the doctor enlarges the image by touching the image or using an enlarge icon of the user interface, the camera 211 zooms in. On the contrary, if the doctor reduces the image displayed on the screen, the camera 211 zooms out. Likewise, the illumination unit 212 of the 1$^{st}$ terminal 210 can be controlled using an illumination icon of the user interface. Thus, the camera 211 is controlled by the control unit 233 of the 2$^{nd}$ terminal 230.

Referring to FIG. 18, if a doctor applies an input through a user interface provided to the screen of the 2$^{nd}$ terminal 230, a guide line for guiding a position of a medically examined part in an image captured by the camera 211 is provided to the screen of the 1$^{st}$ terminal 210. And, a voice guide (e.g., 'place your arm on a yellow region') is also outputted through the speaker 216. If a doctor applies an input through the user interface, the 2$^{nd}$ terminal 230 displays at least one of a scale and lattice for determining a size of the medically examined part on the image captured by the camera 211. Thus, since a size of the medically examined part can be measured using the guide line, scale and lattice for the shape of the medically examined part, a diagnosis can be more accurately made using the image captured by the camera 211.

Figure 19:
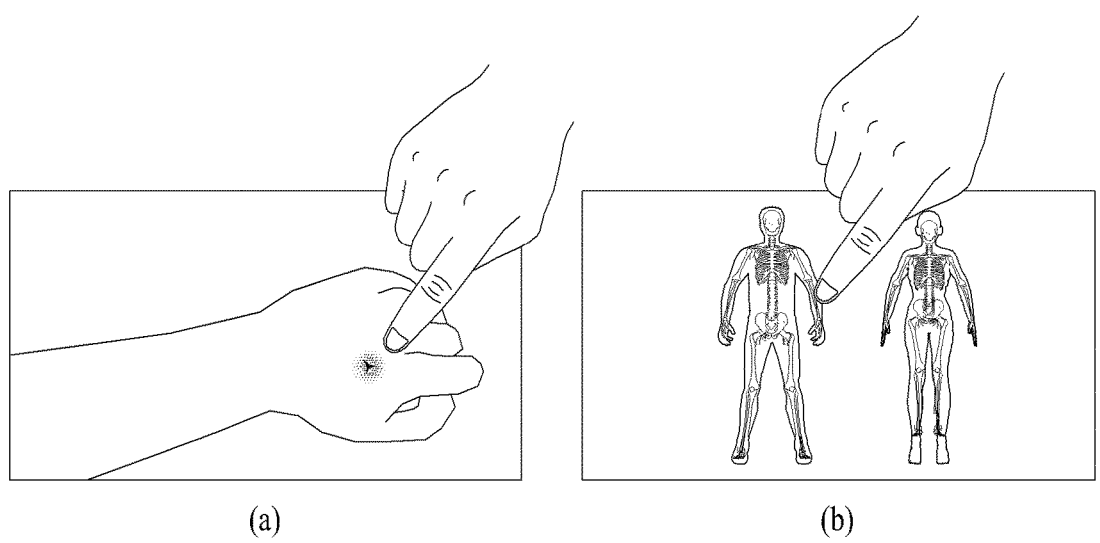
FIG. 19 is a diagram to describe an electronic blackboard function of a $1^{st}$ terminal.

FIG. 19 is a diagram to describe an electronic blackboard function of the 1st terminal 210.

Referring to FIG. 19, while an image captured by the camera 211 is provided to the 2$^{nd}$ terminal 230 of after the image captured by the camera 211 has been saved in the memory 213, a user is able to point at an actually painful part in a photo or image displayed on the screen of the 1$^{st}$ terminal 210 using a finger, a pen or the like. In doing so, if the user points at the screen of the 1$^{st}$ terminal 210 with a finger, a pen or the like, the display 217 recognizes the pointing action and the actually painful part is displayed on the screen of the 2$^{nd}$ terminal [FIG. 19 (a)]. Moreover, in case of a part (e.g., a rib, an internal organ, etc.) actually unavailable for a photo or image, a human photo saved in the memory 213 is displayed on the screen of each of the 1$^{st}$ terminal 210 and the 2$^{nd}$ terminal 230, the user is able to point at a painful part using a finger, a pen or the like [FIG. 19 (b)].

Figure 20:
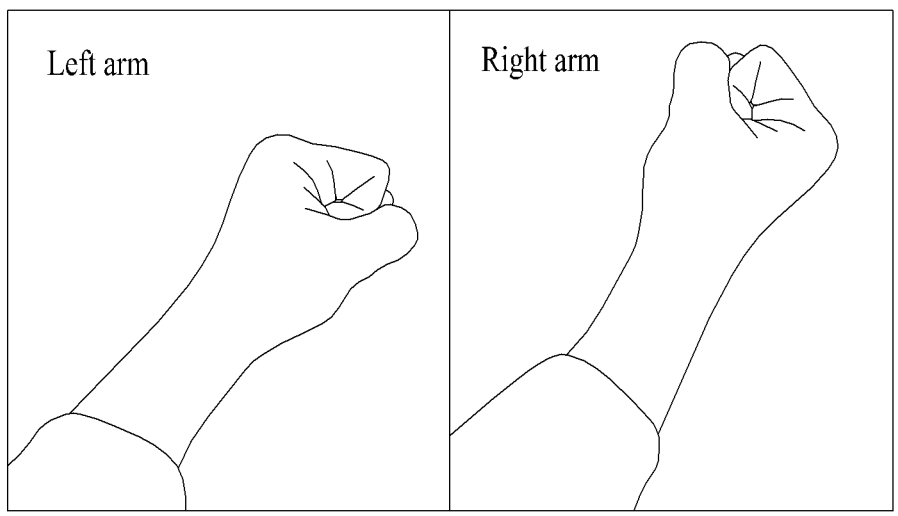
FIG. 20 is a diagram to describe a multi-photographing function of a $2^{nd}$ terminal.

FIG. 20 is a diagram to describe a multi-photographing function of the 2$^{nd}$ terminal 230.

Referring to FIG. 20, the 2$^{nd}$ terminal 230 partitions its screen and is then able to provide both a previously photographed photo/image and a currently photographed photo/image at the same time. And, the 2$^{nd}$ terminal 230 is also able to provide both a user's photo/image and a photo/image of another patient at the same time. Hence, a doctor is able to check whether a user's symptom has been improved or compare the user's symptom to another patient's symptom.

Figure 21:
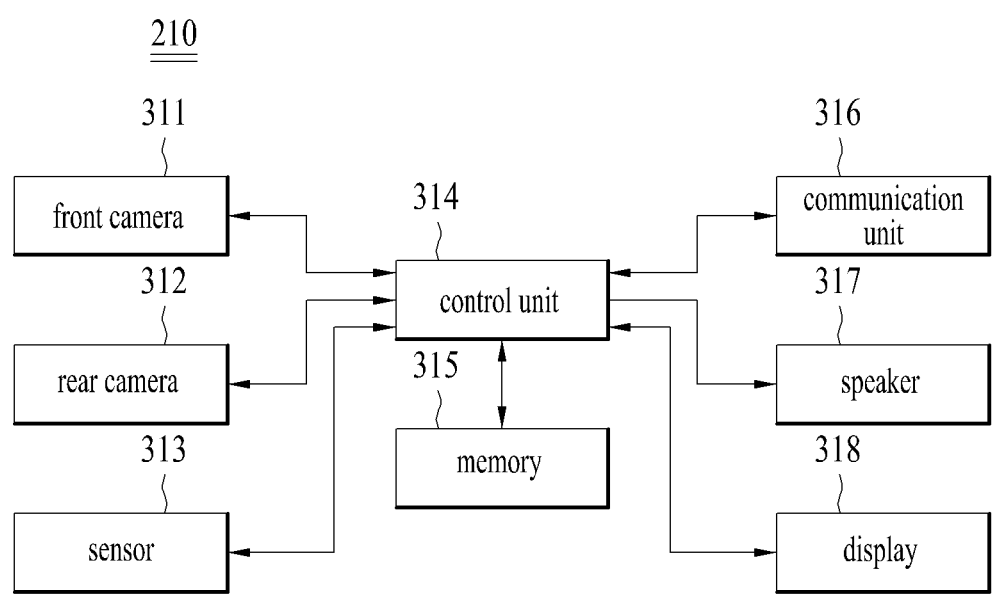
FIG. 21 is a block diagram for another example of a $1^{st}$ terminal.

FIG. 21 is a block diagram for another example of the 1$^{st}$ terminal 210.

Referring to FIG. 21, the 1$^{st}$ terminal 210 may include a front camera 311, a rear camera 312, a sensor 313, a control unit 314, a memory 315, a communication unit 316, a speaker 317 and a display 318. And, the 1$^{st}$ terminal 210 may further include an illumination unit (not shown in the drawing) for camera illumination. In this case, the memory 315, the communication unit 316, the speaker 317 and the display 318 have the same configurations of the components of the former 1$^{st}$ terminal 210 shown in FIG. 13.

The front camera 311 is provided to a front side of the 1$^{st}$ terminal 210 together with the display 318, whereas the rear camera 312 is provided to a rear side of the 1$^{st}$ terminal 210. Each of the front camera 311 and the rear camera 312 is configured to photograph a photo and a video.

The sensor 313 includes a gyro sensor configured to detect an inclination of the 1$^{st}$ terminal 210. The inclination detected by the sensor 313 is provided to the control unit 314. Subsequently, the control unit 314 selects one of the front camera 311 or the rear camera 312 depending on the detected inclination. In particular, the control unit 314 determines whether the 1$^{st}$ terminal 210 is placed in a state approximately parallel with a ground or a state approximately vertical to the ground. If the 1$^{st}$ terminal 210 is placed in the state approximately parallel with the ground, the control unit 314 selects the rear camera 312. If the 1$^{st}$ terminal 210 is placed in the state approximately vertical to the ground, the control unit 314 selects the front camera 311. Subsequently, the control unit 314 controls the selected camera to capture an image. For instance, if the selected camera includes the rear camera 312, it captures a foot closer to the ground. For another instance, if the selected camera includes the front camera 311, it captures a user's face.

The control unit 314 determines whether to control the selected camera to stay in on-state or to be switched to the unselected camera depending on a color of the image captured by the selected camera. For instance, if the image captured by the selected camera includes a preset color (e.g., a skin color, etc.), the control unit 314 keeps the image capture through the selected camera. For another instance, if the image captured by the selected camera does not include a preset color (e.g., a skin color, etc.), the control unit 314 captures an image by switching to the unselected camera.

Subsequently, the control unit 314 determines whether to keep using the switched camera depending on a color of the image captured by the switched camera. Likewise, if the image captured by the switched camera includes the preset color, the control unit 314 keeps the image capture through the switched camera. If the image does not include the preset color, the control unit determines that there is no human body part in the image captured by each of the front camera 311 and the rear camera 312 and then informs a user of it.

Thus, while a video diagnosis is in progress, a user's front/rear camera is switched to another depending on an inclination and a presence or non-presence of a medically examined part is determined, whereby user's convenience can be enhanced.

One example of a first-aid treatment guide using the remote photographing system shown in FIG. 12 is described as follows.

First of all, an image of a medically examined part captured by the camera 211 of the 1$^{st}$ terminal 210 is transmitted to the 2$^{nd}$ terminal 230 by real time and is outputted to the screen of the 1$^{st}$ terminal 210 and the screen of the 2$^{nd}$ terminal 230 by real time as well. A doctor checks the medically examined part of a user through the 2$^{nd}$ terminal 230 by real time. If a further diagnosis is required, the doctor controls the camera 211 to photograph the medically examined part of the user.

The photographed image is saved in each of the 1$^{st}$ terminal 210 and the 2$^{nd}$ terminal 230. In doing so, the 2$^{nd}$ terminal 230 automatically searches for a 1$^{st}$-aid treatment guide corresponding to symptoms of the user based on the saved image and then displays the found first-aid treatment guide on the screen. If the doctor confirms and selects the first-aid treatment guide proposed by the 2$^{nd}$ terminal 230, the 2$^{nd}$ terminal 230 transmits the selected first-aid treatment guide to the 1$^{st}$ terminal 210. Thereafter, the user is able to apply a first-aid treatment by referring to the transmitted first-aid treatment guide. Thus, the first-aid treatment guide is provided to the user by real time, whereby the first-aid treatment can be applied quickly and appropriately.

Another example of a remote photographing system for a video diagnosis according to the present invention is described in detail with reference to FIG. 22 as follows.

Figure 22:
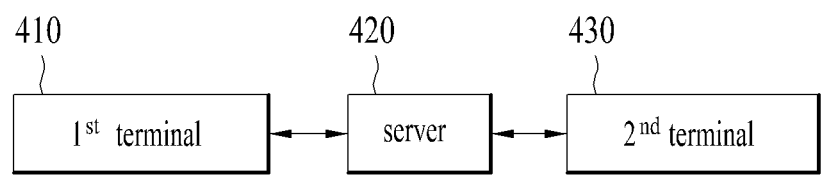
FIG. 22 is a diagram for another example of a remote photographing system for a video diagnosis according to the present invention.

FIG. 22 is a diagram for another example of a remote photographing system for a video diagnosis according to the present invention.

Referring to FIG. 22, a remote photographing system according to the present invention may include a 1$^{st}$ terminal 410, a server 420 and a 2$^{nd}$ terminal 430.

The 1$^{st}$ terminal 410 is a terminal of a user intending to have a medical examination and treatment. The 1$^{st}$ terminal 210 preferably includes such a mobile terminal capable of wireless communication as a smartphone, a laptop, a tablet and the like, by which the present invention may be non-limited. And, the 1$^{st}$ terminal 410 may include a terminal capable of wired communication. Regarding primary functions, the 1$^{st}$ terminal 210 photographs an image of a body part to be diagnosed and then transmits it to the server 420. In doing so, the 1$^{st}$ terminal 410 transmits the photographed image together with user identification information including at least one of a name, social security number (or ID) and phone number of a user.

The server 420 is provided to patients' health care and management and stores diseases and symptoms per patient, a video diagnosis history per patient, a prescription information per patient and the like. The server 420 handles the image transmitted from the 1$^{st}$ terminal 410 through an image pre-processing in response to a request made by the 1$^{st}$ terminal 410 and automatically analyzes an image pattern of an affected part/wound included in the image. The server 420 checks pre-stored data related to a corresponding user using the user identification information provided together with the transmitted image and then compares the image pattern to the pre-stored data. Moreover, the image pattern can be compared to other's data saved in the server 420.

The 2$^{nd}$ terminal 430 receives the analysis result of the server 420 and the provides it to a doctor through a screen. The doctor checks a similar diagnosis history of the corresponding user through the server 420 and is then able to confirm a time, cause, part, user's state & features, prescription history, recovery period and the like of the same symptom. Moreover, the doctor can check an image, case, prescription history, treatment remedy and the like of another patient previously having a symptom similar to that of the corresponding user through the server 420.

Through a series of the above-mentioned processes, the image including the affected part/wound is automatically analyzed by real time. The user searches the server 420 for his own similar cases or other's similar cases and is then able to submit it to the doctor. Moreover, the doctor can make an accurate diagnosis and prescription through previous cases.

It will be appreciated by those skilled in the art that the present invention can be specified into other form(s) without departing from the spirit or scope of the inventions.

It will be appreciated by those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method for managing medicine taking in a system comprising a user terminal, a server, and a medicine container, wherein the method is performed by the user terminal comprising a mobile terminal that comprises a controller operably coupled to a short range wireless communication unit, a detection unit, a communication unit, a memory, a display, and a microphone, the method comprising:
   detecting, via the detecting unit, identification information of a medicine inscribed on the medicine container, the detecting unit comprising at least a camera or a bar code scanner;
   transmitting, via the communication unit, the detected identification information to a server;
   receiving, via the communication unit, medicine taking information corresponding to the detected identification information from the server;
   transmitting, via the short range wireless communication unit, the received medicine taking information to the medicine container;
   setting, by the controller, a medicine taking schedule of a user in accordance with the medicine taking information;
   storing, in the memory, the set medicine taking schedule;
   comparing, by the controller, a time for taking the medicine according to the set medicine taking schedule and average time at which the user has actually taken the medicine;
   adjusting, by the controller, the set medicine taking schedule based on a difference between the time according to the set medicine taking schedule and the average time;
   transmitting, via the communication unit or the short range wireless communication unit, the adjusted medicine taking schedule to the server and the medicine container;
   displaying, via the display, a notification notifying time to take the medicine; and
   determining, by the controller, that the user has taken the medicine in response to a user input or an output signal generated from a sensor of the medicine container, the output signal generated when a lid of the medicine container is open or closed, and the user input comprising a user input received via a user interface displayed on the display or a user's voice received via the microphone.

2. The method of claim 1, further comprising:
   outputting an alarm for informing the user of a time for taking the medicine in accordance with the set medicine taking schedule.

3. The method of claim 1, further comprising:
   determining a presence or non-presence of the medicine taking of the user in accordance with the set medicine taking schedule.

4. The method of claim 3, further comprising:
   outputting a voice message for asking the user of the presence or non-presence of the medicine taking at a medicine taking time designated in accordance with the medicine taking schedule; and
   determining the presence or non-presence of the medicine taking of the user by recognizing a voice of the user.

5. The method of claim 3, further comprising:
   recording, by the user terminal, information with regard to the presence or non-presence of the medicine taking of the user; and
   transmitting, to the server, the information with regard to the presence or non-presence of the medicine taking of the user.

6. The method of claim 1, further comprising:
   outputting an alarm for informing the user of an expiration date of the medicine.

7. The method of claim 1, wherein the medicine container comprises a wireless communication unit configured to wirelessly communicate with the communication unit of the user terminal.

8. The method of claim 7, wherein the medicine container further comprises a display.

9. The method of claim 8, wherein the medicine container further comprises a speaker.

10. The method of claim 9, wherein the medicine container further comprises a memory.

11. The method of claim 1, wherein the mobile terminal comprises a smartphone, a laptop, or a tablet.

12. The method of claim 1, wherein:
    the user terminal directly communicates with the server and the medicine container; and
    the server and the medicine container are not capable of communicating directly with each other.

13. The method of claim 1, further comprising transmitting, via the communication unit, user identification information corresponding to the user to the server.

14. A mobile terminal configured to communicate with a medicine container and a server in a system comprising the mobile terminal, the medicine container, and the server, the mobile terminal comprising:
    a display;
    a detecting unit configured to detect identification information of a medicine inscribed on the medicine container, the detecting unit comprising at least a camera or a bar code scanner;
    a communication unit configured to transceive information;
    a short range wireless communication unit;
    a memory;
    a microphone; and
    a controller operatively coupled to the display, the detecting unit, the short range wireless communication unit, the memory, the microphone, and the communication unit, the controller configured to:
       cause the communication unit to transmit the detected identification information to the server;

cause the communication unit to receive, from the sever, medicine taking information corresponding to the detected identification information;

cause the short range wireless communication unit to transmit the received medicine taking information to the medicine container;

set a medicine taking schedule of a user in accordance with the medicine taking information;

cause the memory to store the set medicine taking schedule;

compare a time for taking the medicine according to the set medicine taking schedule and average time at which the user has actually taken the medicine;

adjust the set medicine taking schedule based on a difference between the time for taking the medicine according to the set medicine taking schedule and the average time;

cause the communication unit or the short range wireless communication unit to transmit the adjusted medicine taking schedule to the server and the medicine container;

cause the display to display a notification notifying time to take the medicine; and determine that the user has taken the medicine in response to a user input or an output signal generated from a sensor of the medicine container, the output signal generated when a lid of the medicine container is open or closed, and the user input comprising a user input received via a user interface displayed on the display or a user's voice received via the microphone.

* * * * *